United States Patent [19]
Hasse

[11] Patent Number: 5,769,833
[45] Date of Patent: *Jun. 23, 1998

[54] DIAPER HAVING PERFUME ZONES

[76] Inventor: Margaret Henderson Hasse, The Procter & Gamble Company, Winton Hill Technical Center 6100 Center Hill Ave., Cincinnati, Ohio 45224

[*] Notice: The term of this patent shall not extend beyond the expiration date of Pat. No. 5,591,146.

[21] Appl. No.: 764,817

[22] Filed: Dec. 12, 1996

[51] Int. Cl.$^6$ ............................ A61F 13/15; A61F 13/20
[52] U.S. Cl. ...................................... 604/359; 604/385.1
[58] Field of Search ..................................... 604/358, 359, 604/360, 385.1, 389

[56] References Cited

U.S. PATENT DOCUMENTS

| | | | |
|---|---|---|---|
| 4,186,743 | 2/1980 | Steiger | 604/359 |
| 4,237,591 | 12/1980 | Ginocchio | 604/359 |
| 4,606,956 | 8/1986 | Charbonneau et al. | 428/40 |
| 4,753,643 | 6/1988 | Kassai | 604/359 |
| 5,290,268 | 3/1994 | Oliver et al. | 604/359 |
| 5,306,487 | 4/1994 | Karapasha et al. | 604/359 |
| 5,429,628 | 7/1995 | Trinh et al. | 604/359 |
| 5,462,538 | 10/1995 | Korpman | 604/359 |
| 5,575,784 | 11/1996 | Ames-Ooten et al. | 604/389 |
| 5,591,146 | 1/1997 | Hasse | 604/359 |

FOREIGN PATENT DOCUMENTS

2271720  4/1994  United Kingdom .................. 604/359

Primary Examiner—Robert A. Clarke
Assistant Examiner—Tram Anh T. Nguyen
Attorney, Agent, or Firm—Theodore P. Cummings; Steven W. Miller; Jacobus C. Rasser

[57] ABSTRACT

The present invention relates to an absorbent article and preferably a diaper or incontinent device having perfume zones disposed on the backsheet outer surface or on a backing member attached to the backsheet outer surface. The perfume zones generally comprise a binder having release agents of one or more types dispersed therethrough. Additionally, the perfume zones contain pull-strips attached to the binder which, when detached from the binder, will cause perfume to be released from the release agents either by shearing of the agents or diffusion as a result of uncovering the binder. The perfume provides the functions of either masking and/or absorbing malodors and are released via fragrance burst, and/or diffusion over time. Furthermore, perfume is released either at attachment of the article about a wearer, at removal of the article from about a wearer and/or during sustained wear of the article about a wearer.

6 Claims, 5 Drawing Sheets

DIAPER HAVING PERFUME ZONES

FIELD OF THE INVENTION

The present invention relates to an absorbent article that has perfume zones on the outer surface of its backsheet. The perfume zones generally comprise a binder having perfume release agents therein. The binder is attached to the outer surface of the absorbent article backsheet or attached to a separate backing member. A pull-strip covers the opposite surface of the binder, thus covering the release agents therein. When the pull-strip is detached, the release agents provide a fragrance burst and/or a diffuse release of perfume.

BACKGROUND OF THE INVENTION

A wide variety of fluid absorbent structures known in the art absorb body fluids such as blood, urine, menses, and the like, and are sanitary and comfortable in use. Disposable products of this type generally comprise fluid-permeable topsheet material, a fluid absorbent core, and fluid-impermeable backsheet material. Various shapes, sizes and thicknesses of such articles have been explored in an attempt to make their use more comfortable and convenient.

Odor control in sanitary products has been under investigation for many years. Many body fluids have an unpleasant odor, or develop such odors when in contact with air and/or bacteria for prolonged periods.

Various odor-controlling agents have been disclosed in the literature. For example, U.S. Pat. No. 4,525,410, Hagiwara, et al., issued Jun. 25, 1985, teaches zeolite particles (doped with bactericidal cations) stably held in a fibrous web by incorporating some portion of meltable fibers in the web, and applying heat. Hagiwara, et al. teaches using these compositions as the outside cover layer in general sanitary goods.

U.S. Pat. No. 2,690,415, F. A. Shuler, issued Sep. 28, 1954, teaches particles of odor-absorbing materials uniformly affixed at the interstices of a permeable web by adhesive to provide an odor absorbent medium, e.g., in catamenials. Particulate carbon, silica gel and activated alumina are noted. Shifting and/or displacement of the particulates is avoided and the sheet is flexible.

U.S. Pat. No. 5,429,628 issued on Jul. 4, 1995 to Trinh, et al. teaches the incorporation of odor absorbing or fragrance releasing particles in the absorbent core or topsheet of an absorbent article. The particles are preferably activated by the presence of moisture from a user through the topsheet and absorbent core.

ABSCENTS (odor-control molecular sieve from Union Carbide) for use in diapers and catamenials are specifically noted in Union Carbide brochure (A. J. Gioffre 1988). The brochure indicates that Union Carbide's market research shows potential benefits in such products. U.S. Pat. Nos. 4,795,482 and 4,826,497, relate to ABSCENTS used as an odor-controlling agent, generally, and in sanitary products, in particular.

SUMMARY OF THE INVENTION

Accordingly, the present invention provides a diaper comprising a fluid pervious topsheet, a fluid impervious backsheet having an inner surface and an outer surface The backsheet is joined to the topsheet, and an absorbent core is located between the topsheet and the backsheet. There is at least one perfume zone located on the outer surface of the backsheet. The perfume zone comprises a binder, having release agents therein, that is attached to the outer surface of the backsheet. Also, the perfume zone comprises a pull-strip that is attached to the backsheet outer surface via the binder having release agents dispersed therein. Preferably, the pull-strip substantially covers the binder. Also, the release agents herein are preferably microcapsules of one or more functions and/or types; i.e., for fragrance burst, diffusion or malodor absorption. Preferably, the perfume release, odor masking and/or odor absorbing functions of the release agents are not activated until the pull-strip member has been released.

In another embodiment herein, a perfume zone additionally comprises a backing member which is attached to the outer surface of the backsheet. The binder is then attached, i.e., coated onto the backing member having release agents dispersed therein, and a pull-strip is attached to the backing member with the binder therebetween.

In a preferred embodiment of the pull-strips herein, the edges of the pull-strip extend beyond the edges of the binder. Further, those extended pull-strip edges are sealed to the outer surface of the backsheet and/or the backing member such that a continuous or nearly continuous seal is formed about the binder.

The release agents comprise perfume selected from the group consisting of uncomplexed cyclodextrins, volatile perfumes, fragrances, essences, zeolites, activated carbons and mixtures thereof In the invention herein, one or more pull-strips may be detached during at least one of three times; i.e., at attachment of a diaper about a wearer, at detachment of a diaper from a wearer and during sustained wear of a diaper.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

As used herein, the term "diaper" refers to an absorbent article generally worn by infants and incontinent persons that is worn about the lower torso of the wearer which absorbs and contains body exudates, and, more specifically, refers to devices which are placed against or in proximity to the body of the wearer. The term "disaposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). The term "perfume" or "encapsulated agents" as used herein refers to odor absorbing and/or masking agents which include volatile perfumes, essences, fragrances, zeolites, activated carbon, cyclodextrins, mixtures thereof and the like which are placed in release agents like microcapsules that are subsequently burst by mechanical shearing forces and/or uncovered to release the perfume as a result of diffusion. The term "release agent" as used herein refers to any suitable means known in the art for the containment and release of perfume as described herein. The term "microcapsules" or "microspheres" as used herein refers to a type of release agent and/or containment assembly for holding and later distributing perfume. The term "perfume-filled" as used herein refers to release agents that are at least partially filled with perfume as defined herein. The term "fragrance burst" as used herein refers to the immediate release of perfume resulting from bursting or uncovering release agents that contain perfume. The term "diffuse" or "steady-state" as used herein refers to a substantially continuous release of perfume from a release agent. By the term "embedded" it is meant herein the integration or securement of one material within another material, adjacent to another material, and/or onto another material, e.g., release agents embedded within a binder.

Preferably, the release agents for all embodiments disclosed herein are one of several types of microcapsules disclosed herein. In the type of microcapsule that is sheared or ruptured, at least one opening will be created on the surface of the previously unopened microcapsule through which perfume will diffuse through one of the mechanisms disclosed herein (e.g., fragrance burst, steady-state diffusion, etc.). Alternatively, the microcapsule can be a porous, substantially filled-in structure that releases perfume through one or more disclosed mechanisms as the microcapsule is uncovered and therefore exposed to the atmosphere. By the term "uncovered" it is meant herein that a structure, which had been previously substantially covered and/or fully enclosed from exposure to the air by a covering means, is now exposed; e.g., wherein the pull-strip member herein substantially covers the release agents embedded within a perfume zone. Also alternatively, at least a plurality of microcapsules herein absorb odors in addition to or rather than emitting perfume via the mechanisms disclosed herein such as in a fragrance burst.

Figure 1:
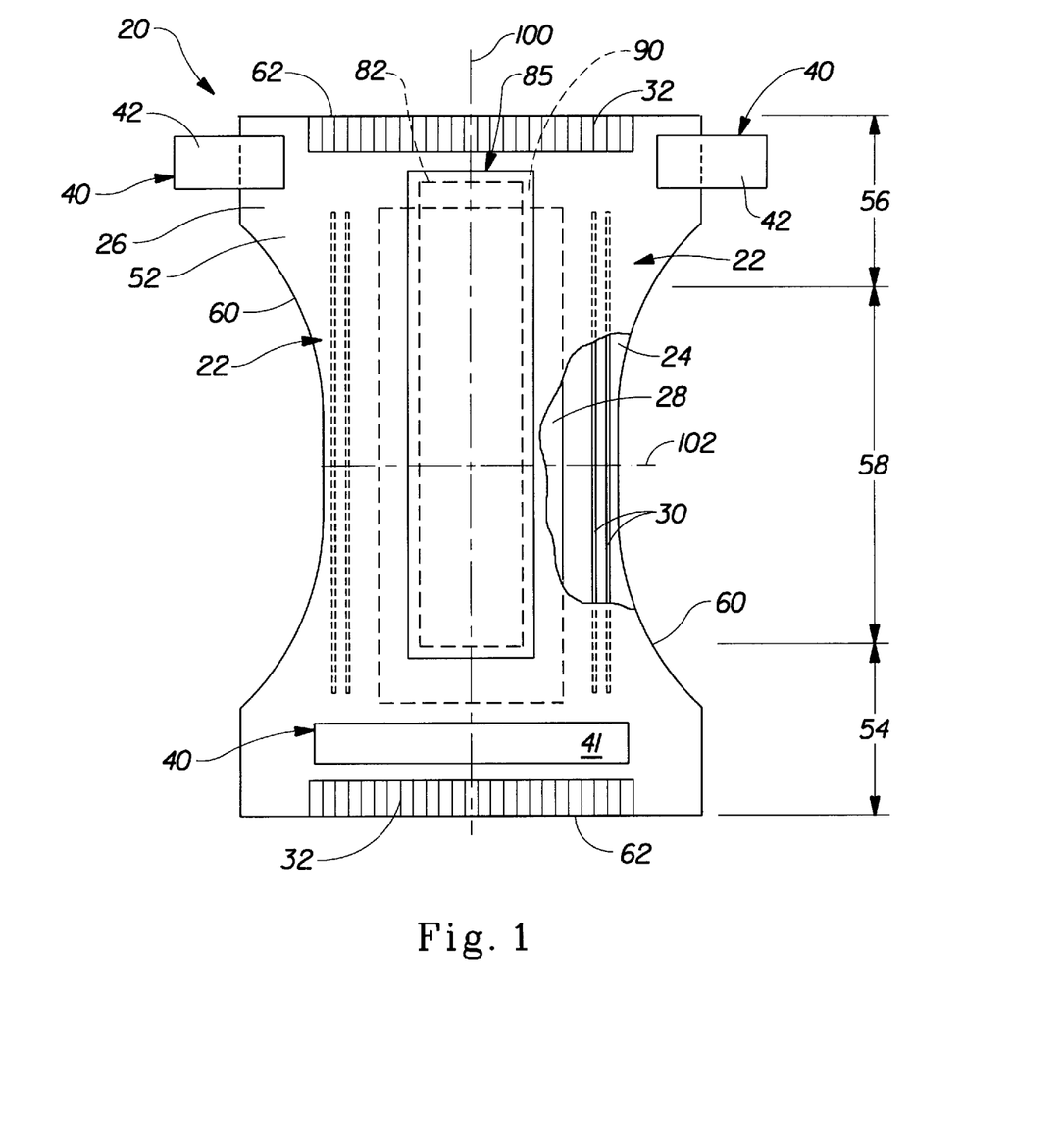
FIG. 1 is a plan view of a disposable diaper embodiment of the present invention having portions cut-away to reveal underlying structure, the outer surface of the diaper facing the viewer.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces away from the wearer, the outer surface 52, facing the viewer. As shown in FIG. 1, the diaper 20 comprises a containment assembly 22 preferably comprising a liquid pervious topsheet 24, a liquid impervious backsheet 26 joined to the topsheet 24, and an absorbent core 28 positioned between the topsheet 24 and the backsheet 26. The diaper preferably further comprises elasticized leg cuffs 30; elasticized waistbands 32; a fastening system 40 comprising a pair of first fastening members 42 and a second fastening member 41.

The diaper 20 is shown in FIG. 1 to have an outer surface 52 (facing the viewer in FIG. 1), an inner surface 50 (not shown) opposed to the outer surface 52, a front waist region 54, a rear waist region 56 longitudinally opposed to the front waist region 54, a crotch region 58 positioned between the front waist region 54 and the rear waist region 56, and a periphery which is defined by the outer perimeter or edges of the diaper 20 in which the longitudinal edges are designated 60 and the end edges are designated 62. The inner surface 50 of the diaper 20 comprises that portion of the diaper 20 which faces toward the wearer's body during use (i.e., the inner surface 50 is generally formed by at least a portion of the topsheet 24 and other components joined to the topsheet 24). The outer surface 52 of the diaper 20 comprises that portion of the diaper 20 which faces away from the wearer's body during use (i.e., the outer surface 52 is generally formed by at least a portion of the backsheet 26 and other components joined to the backsheet 26). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The front waist region 54 and the rear waist region 56 extend from the end edges 62 of the periphery to the crotch region 58.

The diaper 20 also has two centerlines, a longitudinal centerline 100 and a transverse centerline 102. The term "longitudinal", as used herein, refers to a line, axis, or direction in the plane of the diaper 20 that is generally aligned with (e.g., approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction which divides the wearer into front and back body halves.)

The containment assembly 22 of the diaper 20 is shown in FIG. 1 as comprising the main body (chassis) of the diaper 20. The containment assembly 22 comprises at least an absorbent core 28 and preferably an outer covering layer comprising the topsheet 24 and the backsheet 26. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a backsheet, and an absorbent core.) For unitary absorbent articles, the containment assembly 22 comprises the main structure of the diaper with other features added to form the composite diaper structure. Thus, the containment assembly 22 for the diaper 20 generally comprises the topsheet 24, the backsheet 26, and the absorbent core 28.

FIG. 1 shows a preferred embodiment of the containment assembly 22 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge", which issued to Kenneth B. Buell, et al. on Sep. 29, 1992; each of which is incorporated herein by reference.

Figure 1A:
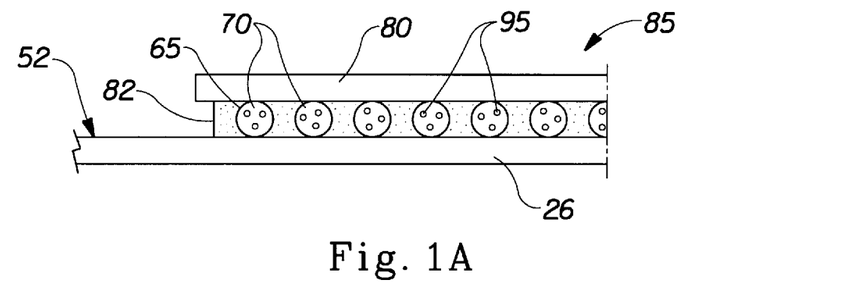
FIG. 1A is a side view of one type of perfume zone described herein.
Figure 1B:
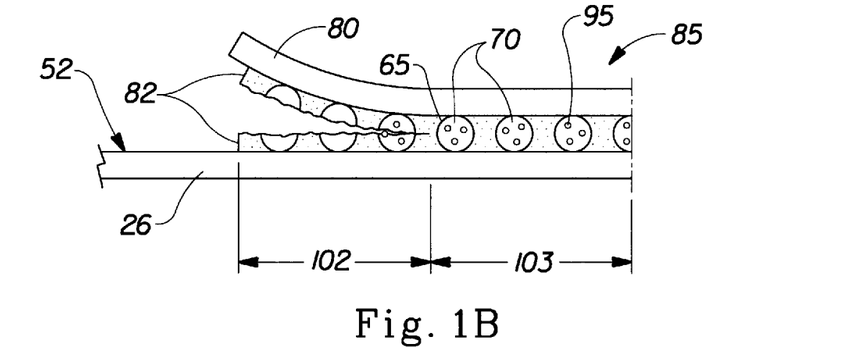
FIG. 1B is a side view of the perfume zone in FIG. 1A during disengagement of the pull-strip from the perfume zone.

In a preferred embodiment, FIGS. 1A and 1B show that the microcapsule containing binder 82 is attached directly to the outer surface 52 or garment surface of the backsheet 26. The pull-strip 80 is laid directly over the binder 82 and is attached thereto. The pull-strip 82 will preferably fully cover the binder 82. In a preferred application of all of the embodiments disclosed herein, the pull-strip 80 will not only fully cover the binder 82 but also will have edges that extend beyond the edges of the binder 82. The extended edges of the pull-strip 80 will preferably be attached directly to the opposed surface of either the outer backsheet surface 52 (see FIGS. 1A and 1B) or the backing member 88 (see FIGS. 2A and 2B), thus forming a continuous or semi-continuous seal about the entire binder 82. This preferred sealing serves to restrict the release of any one of the perfumes disclosed herein and to protect the binder 82 and microcapsules 70 from outside substances, e.g., water, dirt, and to provide the greatest possible perfume release at the user's discretion. In one embodiment, the extended edges of the pull-strip 80 are attached to the backsheet outer surface 52 or backing member 88 by an adhesive. In another example of the above attachment, a vacuum seal is formed using the extended edges of the pull-strip 80 to seal the binder 82.

Figure 2:
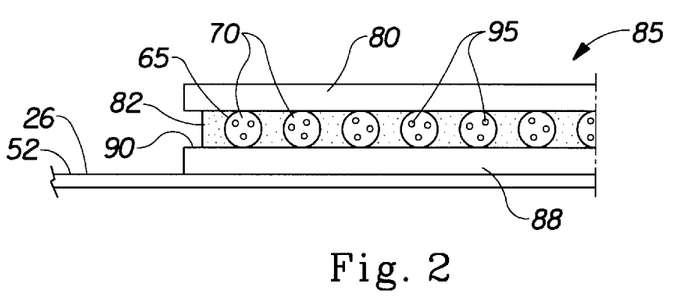
FIG. 2 is a side view of another type of perfume zone herein showing one type of microcapsule prior to disengagement of the pull-strip from the perfume zone.
Figure 2A:
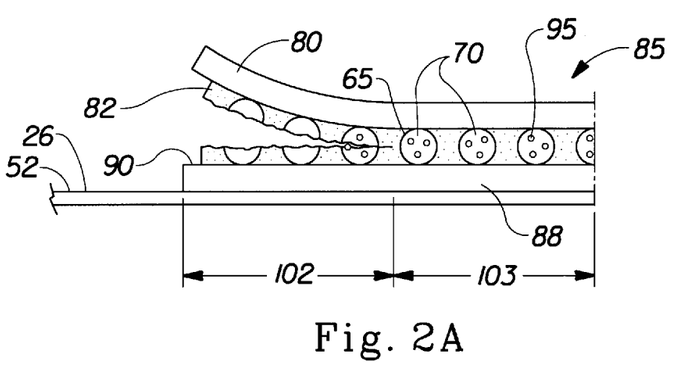
FIG. 2A is a side view of the perfume zone shown in FIG. 2 at disengagement of the pull-strip from the perfume zone.

In another alternative embodiment, FIGS. 2 and 2A disclose in part a perfume zone 85 comprising a backing member 88 attached directly to the outer surface 52 of the backsheet 26. That is, the backing member 88 is an independent member attached directly to the backsheet outer surface 52 that is preferably not removable upon separation of the pull-strip 80 from the binder 82. Additionally, the perfume zone 85 comprises a micro-encapsulated binder 82 that is attached to the backing member surface and attached to a pull-strip 80 on the opposite surface. By the term "micro-encapsulated", it is meant herein that the binder comprises a plurality of microcapsules therein. The binder 82 is secured to the perfume surface 90 and attaches the pull-strip 80 to the backing member 88. The binder 82 preferably substantially comprises a plurality of release agents 65, preferably being microcapsules 70, that are activated upon release of the pull-strip 80 from the perfume zone 85. By activated it is meant herein that release agents 65 are sheared to release perfume and/or uncovered to release perfume by any one of the mechanisms discussed herein (e.g., by fragrance burst).

The invention herein comprises two methods by which malodors can be at least partially subdued. They are odor masking and odor absorbing. Two mechanisms which provide odor masking are perfume release through a fragrance burst or perfume diffusion over time. When perfume is released by either of these two methods, malodors tend to be masked by perfume of greater intensity. The intensity or strength of the perfume forms no part of the invention but is increased or decreased at the discretion of a manufacturer. In contrast, odor absorbers such as cyclodextrin or activated carbon serve to lock malodors into their molecular structures in such fashion that the malodor molecules go undetected by most (if not all) human olfactory senses.

FIGS. 1A, 1B, 2 and 2A illustrate schematically one mechanism believed to be the operative one in insuring that a controlled amount of perfume 95 is released from the release agents 65. Referring to the unpeeled portion 103 of the pull-strip 80, it can be seen that a portion of at least some of the microcapsules 70 are at least partially embedded within a non-sticky binder 82. By "non-sticky" binder, it is meant herein that the binder, while causing release agents 65 (e.g., microcapsules 70) to be embedded therein, will substantially not stick to other surfaces such as a wearer's clothing or body when the pull-strip 80 has been released prior to or during wear of a diaper. Specifically, when a diaperer detaches pull-strip 80 and thus uncovers the perfume zone 85 having an exposed non-sticky binder 82 thereon, that binder 82 will not stick to any clothing that is worn adjacent to or over the diaper. Referring now to the peeled portion 102 of the pull-strip 80, it can be seen that the effects of peeling the pull-strip 80 produces a shear force across the tops of the microcapsules 70 that facilitates their rupture, thus releasing the perfume 95 contained therein.

Figure 3:
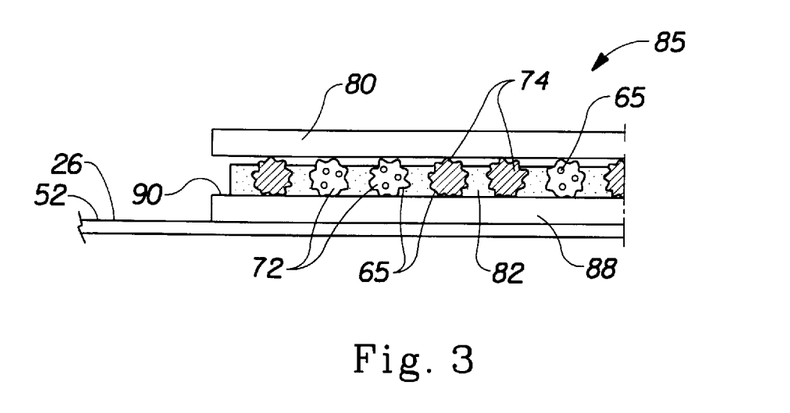
FIG. 3 is a side view of the perfume zone with two types of microcapsules therein prior to disengagement of the pull-strip from the perfume zone.
Figure 3A:
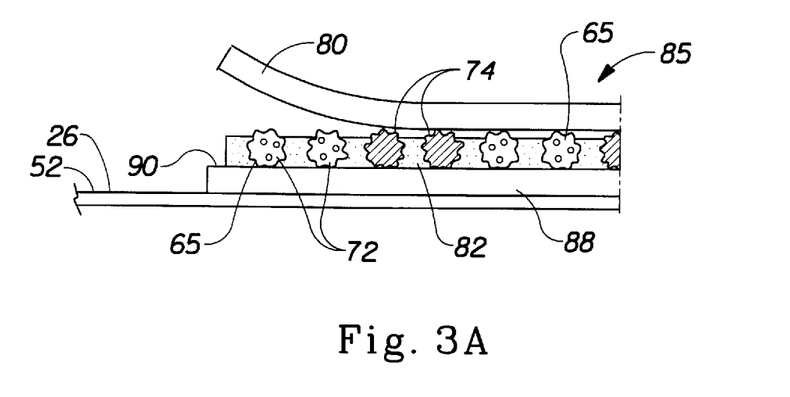
FIG. 3A is a side view of the perfume zone in FIG. 3 at disengagement of the pull-strip from the perfume zone.

Note, FIGS. 1A and 1B disclose the binder 82 being attached directly to the outer surface 52 of the backsheet 26. This is a preferred embodiment. Conversely, FIGS. 2–3A show the binder 82 being attached to a backing member 88. The backing member 88 is an independent member that is attached to the outer surface 52 of the backsheet 26.

Those factors which control the number of microcapsules 70 ruptured and hence the quantity of perfume 95 released are entirely within the control of the manufacturer's discretion through manipulation of such parameters as microcapsule size and wall thickness, type of binder used, quantity of binder used, the amount and type of perfume used, rupture strength of the microcapsules, the number and distribution of the microcapsules, adhesive strength of a binder relative to the rupture strength of the microcapsules, and other such factors that may affect microcapsule rupture. In one example, it is believed that both the force required to detach a pull-strip 80 from a binder 82 should be greater than the force required to rupture a microcapsule embedded within a binder 82. If this condition is met, microcapsules at least partially embedded within the perfume zone 85 by a binder 82 will rupture due to shearing of their outer surfaces. In another example, microcapsules 70 sized at 50 microns or above should readily burst upon separation of the pull-strip 80 from the perfume zone 85 because of increased effects upon adhesive and cohesive properties of a binder 82 in contact with the microcapsules 70.

A binder 82 will preferably form a bond to the surface 90 of the perfume zone 85. In one embodiment, the binder will also have microcapsules 70 that are at least partially embedded therein. A pull-strip 80, preferably comprising polyethylene, polypropylene, a nonwoven, and/or a cellulosic material (these are also suitable materials for the backing member 88), will preferably substantially cover the perfume zone 85. The pull-strip 80 will lay on the side of the binder that is opposite to the surface of the perfume zone 85. The pull-strip 80 will form a bond with the binder 82 such that when the pull-strip is detached, i.e., pulled from the perfume zone 85, microcapsules 70 will rupture, thus providing a fragrance burst. While not wishing to be bound by any particular theory, it is believed that the detachment of the pull-strip 80 shears the rupturable microcapsules 70 at disengagement of the pull-strip from the perfume zone 85, thus releasing their perfume immediately. It is most desirable to have a binder, the absolute cohesive strength of which is less than its adhesive strength to the surface of the perfume zone 85.

In another embodiment herein, the binder 82 at least partially comprises release agents 65 that diffusely release perfume over time, e.g., odor absorbers. As in the previous embodiment, the pull-strip 80 is detached from the binder 82, thus uncovering the release agents 65 therein to exposure to the atmosphere. These types of diffuse release agents may be combined with the shearable/rupturable type of release agents to provide both a fragrance burst and time diffuse release of perfume.

A binder 82 bearing microcapsules 70 can be coated onto a portion of the adhering surface of the perfume zone 85. This binder is preferably the sole bonding material between the pull-strip 80, release agents 65 and perfume surface 90. If any effective amount of adhesive is present in the areas where microcapsules 70 are deposited with the intention of having them removable and not rupture due to separation of the pull-strip 80 from the perfume zone 85, it is then preferable that the cohesive strength of that adhesive be lower than the rupture strength of the microcapsules 70.

FIGS. 3 and 3A illustrate schematically a similar mechanism as in FIGS. 2 and 2A believed to be the operative one in insuring that microcapsules 72 which either diffuse perfume over time or microcapsules 74 which release substances that can absorb malodors are activated. As in FIGS. 2 and 2A, the pull-strip 80 is released from the perfume zone 85, thus uncovering the microcapsules 72 and 74. Microcapsules 72 and 74 are shown here together for simplicity, however, embodiments can comprise any combination of the microcapsule types disclosed herein for any sort of multifunctional purpose; e.g., one embodiment may comprise all three microcapsule types (70, 72 & 74) or may comprise any combination of two types, or only one type. This preference is at the discretion of the manufacturer.

Figure 4:
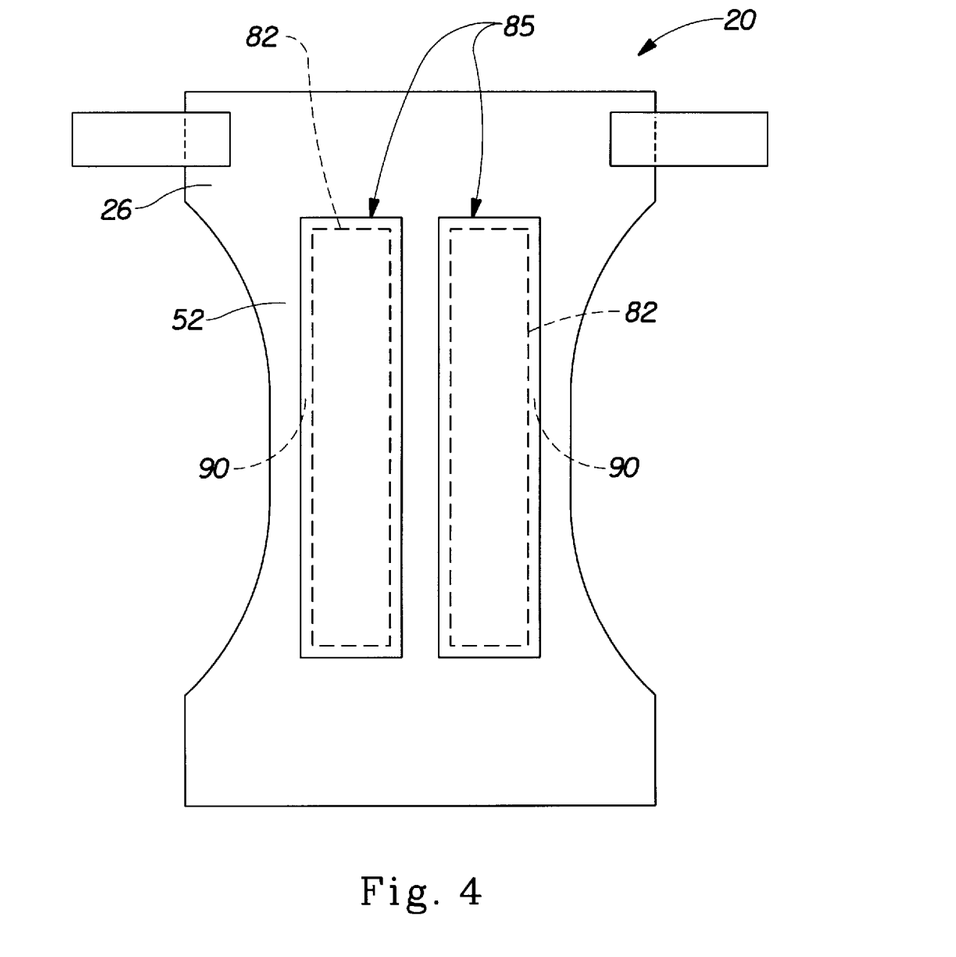
FIG. 4 is a plan view of an alternative embodiment of a disposable diaper the present invention having multiple perfume zones.

FIG. 4 discloses an alternative embodiment in which a plurality of perfume zones 85 may be applied to the outer surface 52 of the backsheet 26 of a diaper 20. There is no fixed number as to how many perfume zones may be applied to a part of the backsheet outer surface 52. The number of perfume zones 85 assigned is entirely within the purview of the manufacturer. A perfume zone 85 may be of any shape and configuration as deemed desirable by a manufacturer. Also, the size of a perfume zone is not fixed but is within the design limitations of a manufacturer. Of course, all sizes, numbers and configurations herein should be compatible and within the limits of the function and size of a diaper.

Referring again to FIG. 1, the diaper 20 also comprises a fastening system 40 having first fastening members 42 preferably comprising fastening tabs and a second fastening member 41 that can attach to one-another to form a side closure which maintains the front waist region 54 and the rear waist region 56 in an overlapping configuration such that lateral tensions are maintained around the circumference of the diaper to maintain the diaper on the wearer. Exemplary fastening systems are disclosed in U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; U.S. Pat. No. 3,848,594 entitled "Tape Fastening System for Disposable Diaper" issued to Buell on Nov. 19, 1974; U.S. Pat. No. 4,662,875 entitled "Absorbent Article" issued to Hirotsu et al. on May 5, 1987; and the herein before referenced U.S. Pat. application Ser. No. 07/715,152; each of which is incorporated herein by reference.

Examples of suitable adhesive tape tab fastening systems are disclosed in U.S. Pat. No. 3,848,594 issued to Buell on Nov. 19, 1974; and U.S. Pat. No. 4,662,875 issued to Hirotsu and Robertson on May 5, 1987; each of which are incorporated herein by reference. Examples of other closure systems, including mechanical closure systems, useful in the present invention, are disclosed in U.S. Pat. No. 4,869,724 issued to Scripps on Sep. 26, 1989; U.S. Pat. No. 4,848,815 issued to Scripps on Jul. 11, 1989; and the two-point fastening system described in U.S. Pat. No. 5,242,436 issued to Weil, Buell, Clear, and Falcone on Sep. 7, 1993; each of which are incorporated herein by reference. When a two-point fastening system is used, the waist closure members of the waist closure system are preferably longitudinally aligned with the extensible front waist feature 42 and laterally aligned with the elastic strands of the extensible leg cuff 30 to provide an effective closure about both the legs and the waist. As shown throughout the disclosure, the diaper 20 may be provided with a pair of fastening tabs 42 that allow the side panels to be first joined together. The diaperer then brings the containment assembly 22 between the legs of the wearer and joins the assembly 22 to the outer layer of the waist feature. Such a configuration and securing method is more fully described in the above-referenced U.S. application Ser. No. 08/044,562 (New, et al.)

The fastening system can comprise any attachment means known in the art including pressure sensitive adhesives, cohesive materials, mechanical fasteners such as hook and loop type fasteners, or any combination of these or any other attachment means known in the art. Exemplary adhesive tape tab fastening systems are disclosed in U.S. Pat. No. 3,848,594 entitled "Tape Fastening System for Disposable Diaper" issued to Buell on Nov. 19, 1974; and U.S. Pat. No. 4,662,875 entitled "Absorbent Article" issued to Hirotsu and Robertson on May 5, 1987. Exemplary fastening systems comprising mechanical fastening components are described in U.S. Pat. No. 5,058,247 entitled "Mechanical Fastening Prong" issued to Thomas Oct. 22, 1991; U.S. Pat. No. 4,869,724 entitled "Mechanical Fastening Systems With Adhesive Tape Disposal Means For Disposal of Absorbent Articles" issued to Scripps on Sep. 26, 1989; and U.S. Pat. No. 4,846,815 entitled "Disposable Diaper Having an Improved Fastening Device" issued to Scripps on Jul. 11, 1989. An example of a fastening system having combination mechanical/adhesive fasteners is described in U.S. Pat. No. 4,946,527 entitled "Pressure-Sensitive Adhesive Fastener and Method of Making Same" issued to Battrell on Aug. 7, 1990. Each of these patents are incorporated herein by reference.

As discussed, one embodiment of the present invention comprises a hook fastening material preferably comprising a base and a plurality of engaging elements extending from the base. The hook fastening material is intended to engage fibrous elements of a loop fastening material so as to provide a secure fastening device. Thus, the hook fastening material may be manufactured from a wide range of materials. Further, the engaging elements may have any shape such as hooks, "T's", "mushrooms" or any other shape as are well known in the art. Suitable materials include nylon, polyester, polypropylene, or any combination of these materials. Examples of preferred hook fastening materials are available from Aplix of Charlotte, N.C. under the trade designation 960, 957 and 942. Other preferred hook fastening materials are available from the Minnesota Mining and Manufacturing Company of St. Paul, Minn. under the trade designations CS200, CS300, MC5 and MC6. Another preferred hook fastening material is described in U.S. Pat. No. 5,058,247 entitled "Mechanical Fastening Prong" issued to Thomas Oct. 22, 1991 which is incorporated herein by reference.

The second fastening member preferably comprises a fastening element engageable with the hook member. Thus, the second fastening member may be manufactured from a wide range of materials and configurations capable of securely engaging the hook member. For example, the second fastening member may comprise identical complementary elements or distinct complementary elements. As used herein, the term "identical complementary elements" is used to define mechanical fastening systems wherein the engaging elements of the hook member and the second fastening member comprise the same configuration or structure that are interlocking. Examples of such systems are described in Brown et al. U.S. Pat. No. 4,322,875 entitled "Two Strip Materials Used For Forming Fasteners" issued on Apr. 16, 1982 and Kellenberger et al. U.S. Pat. No. 4,701,179 entitled "Fixed Position Fasteners For Disposable Absorbent Garments" issued on Oct. 20, 1987. The term "distinct complementary elements" is used herein to designate a system wherein the hook member is different from the second fastening member but is engageable therewith.

In one preferred embodiment, the second fastening component comprises a plurality of fiber elements, such as a loop fastening material, that engage the engaging elements of the hook component. The loop fastening material may be manufactured from a wide range of materials to provide fiber elements, preferably being loops. Suitable materials include woven materials, nonwovens, nylons, polyesters, polypropylenes, or any combination of these materials. One suitable loop fastening material is a nonwoven available from Minn. Mining and Manufacturing Company, St. Paul, Minn. under the trade designation EBL. A preferred loop fastening material comprises a number of shaped engaging elements projecting from a woven backing such as the commercially available material designated Guilford 18904 available from Guilford Mills of Greensboro, N.C. Other suitable loop components are available from the Minn. Mining and Manufacturing Company of St. Paul, Minn. under the trade designation EBL. An inexpensive loop fastening material and a method of making the same is described in U.S. Pat. No. 5,032,122, entitled "Loop Fastening Material For Fastening Device and Method of Making Same" issued to Noel et al., Jul. 16, 1991, which application is incorporated herein by reference. Another suitable loop material is described in U.S. Pat. No. 5,326,612 entitled "Nonwoven Female Component for Refastenable Fastening Device and Method of Making the Same" issued to David J. K. Goulait on Jul. 5, 1994, which is hereby incorporated by reference herein. Yet other suitable second fastening components are described in co-pending U.S. patent application Ser. No. 08/254,814 entitled "Nonwoven Female Component For Refastenable Fastening Device and Method of Making the Same" filed Jun. 6, 1994 in the names of Patrick Jay Allen et al.; U.S. patent application Ser. No. 08/287,571 entitled "Nonwoven Female Component For Refastenable Fastening Device" filed Aug. 9, 1994 in the names of Willie F. King et al.; and U.S. Pat. Ser. No. 08/374,269 entitled "Female Component For Refastenable Fastening Device" filed Jan. 18, 1995 in the names of Carl L. Bergman et al.

The fastening elements may be disposed on either the outer surface 52 or the inner surface 50 of the diaper 20. In a preferred embodiment, however, the fastening elements are disposed on the diaper 20 such that the fasteners do not irritate the wearer's skin. In addition, the fastening elements may either be a discrete separate element affixed to the diaper 20 or a unitary piece of material that is neither divided nor discontinuous with an element of the diaper 20 such as the topsheet 24 or the backsheet 26. While the fastening elements can assume varying sizes and shapes, they preferably comprise one or more separate patches of material joined to the diaper 20 to allow for the best fit for a broad range of wearers.

The topsheet 24 is positioned adjacent the body surface of the absorbent core 28 and is preferably joined thereto and to the backsheet 26 by attachment means (not shown) such as those well known in the art. Suitable attachment means are described with respect to joining the backsheet 26 to the absorbent core 28. As used herein, the term "joined" encompasses configurations whereby a first element is directly secured to a second element by affixing the first element directly to the second element, and configurations whereby the first element is indirectly secured to the second element by affixing the first element to an intermediate member(s) which in turn is affixed to the second element. In a preferred embodiment of the present invention, the topsheet 24 and the backsheet 26 are joined directly to each other in the diaper periphery and are indirectly joined together by directly joining them to the absorbent core 28 by attachment means (not shown).

The topsheet 24 is compliant, soft feeling, and non-irritating to the wearer's skin. Further, the topsheet 24 is liquid pervious permitting liquids (e.g., menses and/or urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

There are a number of manufacturing techniques which may be used to manufacture the topsheet 24. For example, the topsheet 24 may be a nonwoven web of fibers. When the topsheet comprises a nonwoven web, the web may be spunbonded, carded, wet-laid, meltblown, hydroentangled, combinations of the above, or the like. A preferred topsheet is carded and thermally bonded by means well known to those skilled in the fabrics art. A preferred topsheet comprises staple length polypropylene fibers having a denier of about 2.2. As used herein, the term "staple length fibers" refers to those fibers having a length of at least about 15.9 mm (0.625 inches). Preferably, the topsheet has a basis weight from about 18 to about 25 grams per square meter. A suitable topsheet is manufactured by Veratec, Inc., a Division of International Paper Company, of Walpole, Mass. under the designation P-8.

The backsheet 26 is positioned adjacent the garment surface of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat.

No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, heat/pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils). The backsheet preferably comprises a polyethylene blend film of about 0.025 mm (1.0 mil) as is manufactured by Tredegar Corporation of Terre Haute, Ind. and marketed as P8863.

The absorbent core 28 may be any absorbent means which is capable of absorbing and retaining liquids such as urine and other certain body exudates. The absorbent core 28 has a garment surface, a body surface, side edges, and waist edges. The absorbent core 28 may be manufactured in a wide variety of sizes and shapes (e.g., rectangular, hourglass, "T"-shaped, asymmetric, etc.) a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulose fibers, tissue including tissue wraps and tissue laminates, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults. FIG. 1 shows a preferred embodiment of the diaper 20 having a rectangular-shaped absorbent core.

An absorbent structure useful as the absorbent core 28 of the present invention that has achieved wide acceptance and commercial success is described in U.S. Pat. No. 4,610,678 entitled "High-Density Absorbent Structures" issued to Weisman and Goldman on Sep. 9, 1986. U.S. Pat. No. 4,673,402 entitled "Absorbent Articles With Dual-Layered Cores" issued to Weisman, Houghton, and Gellert on Jun. 16, 1987; U.S. Pat. No. 4,888,231 entitled "Absorbent Core Having A Dusting Layer" issued to Angstadt on Dec. 19, 1989; U.S. Pat. No. 5,147,345 entitled "High Efficiency Absorbent Articles For Incontinence Management", issued to Young, LaVon & Taylor on Sep. 15, 1992; U.S. Pat. No. 5,102,597 entitled "Porous, Absorbent, Polymeric Macrostructures and Methods Of Making the Same", issued to Roe, Lahrman and Berg on Apr. 7, 1992; and U.S. Pat. No. 4,834,735, entitled "High Density Absorbent Members Having Lower Density and Lower Basis Weight Acquisition Zones", issued to Alemany and Berg on May 30, 1989; also describe absorbent structures that are useful in the present invention. The absorbent core 28 is preferably the dual-layer absorbent structure described in U.S. Pat. No. 5,234,423 entitled "Absorbent Article With Elastic Waist Feature and Enhanced Absorbency", issued to Alemany and Clear on Aug. 10, 1993. Each of these patents are incorporated herein by reference.

In a preferred embodiment of the present invention, an acquisition layer(s) may be positioned between the topsheet 24 and the absorbent core 28 and joined to the absorbent core 28. The acquisition layer may serve several functions including improving wicking of exudates over and into the absorbent core. There are several reasons why the improved wicking of exudates is important, including providing a more even distribution of the exudates throughout the absorbent core 28 and allowing the absorbent structure to be made relatively thin. The wicking referred to herein may encompass the transportation of liquids in one, two or all directions (i.e., in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of absorbent structures disclosed herein having an acquisition layer and a topsheet are more fully described in U.S. Pat. No. 4,950,264 issued to Osborn, III and U.S. patent application Ser. No. 07/944,764, "Absorbent Article Having Fused Layers", filed Oct. 7, 1992, in the names of Cree, et al. Each of these references are incorporated herein by reference. In a preferred embodiment, the acquisition layer may be joined with the topsheet 24 and separate from the inserted absorbent material or absorbent core 28 by any of the conventional means for joining webs together, most preferably by fusion bonds as is more fully described in the above-referenced Cree application.

The diaper 20 preferably further comprises extensible leg cuffs 30 for providing improved containment of liquids and other body exudates. Each extensible leg cuff 30 may comprise several different embodiments for reducing the leakage of body exudates in the leg regions. (The leg cuff can be and is sometimes also referred to as leg bands, leg flaps, barrier cuffs, or elastic cuffs.) U.S. Pat. No. 3,860,003 entitled "Contractable Side Portions For a Disposable Diaper" issued to Buell on Jan. 14, 1975, describes a disposable diaper which provides a contractible leg opening having a leg flap and one or more elastic members to provide an elasticized leg cuff (gasketing cuff). U.S. Pat. No. 4,909,803 entitled "Disposable Absorbent Article Having Elasticized Flaps" issued to Aziz & Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edge-leakage-guard gutters configured to contain free liquids within the garment. U.S. Pat. No. 5,032,120 entitled "Disposable Absorbent Article Having Improved Leg Cuffs" issued to Freeland & Allen on Jul. 16, 1991, discloses an absorbent article having leg cuffs having a relatively low ultimate contact force at relatively high elongation's accomplished, for example, by low contact force differential material. U.S. Pat. No. 5,087,255 entitled "Absorbent Article Having Inflected Barrier Cuffs" issued to Sims on Feb. 11, 1992, discloses an absorbent article having inflected barrier cuffs with the distal edge positioned outboard of the proximal edge in one waist region and inboard in the other to provide better fit about the hips/buttocks. Each of these patents are incorporated herein by reference.

The diaper 20 further comprises extensible waist features that provide improved fit and containment. The extensible waist features at least extend longitudinally outwardly from the containment assembly 22, preferably a respective waist edge of the absorbent core 28, and generally form at least a portion of the end edge of the diaper 20. While a disposable diaper of the present invention is constructed with an extensible waist feature disposed in each waist region (an elastic waist feature 32), the discussion will focus on diapers having different configurations for each extensible waist feature. At a minimum, it is preferred that the diaper at least have one of the extensible waist features constructed according to the present invention, more preferably at least the elastic waist feature 32. The waist features can be constructed as a separate element joined to the containment assembly 22 or as an extension of other elements of the diaper (i.e., unitary). The waist features will be described with respect to preferred embodiments in which certain portions or panels comprise an extension of other elements of the diaper such as the backsheet 26, the topsheet 24, or both, and other portions or panels comprise a separate element joined to other portions or panels of the waist feature or other panels of the diaper.

As used herein, the term "cyclodextrin" includes any of the known cyclodextrins such as unsubstituted cyclodextrins containing from six to twelve glucose units, especially, alpha-, beta-, and gamma-cyclodextrins, and/or their derivatives, and/or mixtures thereof. The alpha-cyclodextrin consists of 6, the beta-cyclodextrin 7, and the gamma-cyclodextrin 8 glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. These cavities can be filled with all or a portion of an organic molecule with suitable size to form an "inclusion complex." Alpha-, beta-, and gamma-cyclodextrins can be obtained from, among others, American Maize-Products Company (Amaizo), Hammond, Ind.

Cyclodextrin derivatives are disclosed in U.S. Pat. Nos: 3,426,011, Parmerter et al., issued Feb. 4, 1969; 3,453,257, 3,453,258, 3,453,259, and 3,453,260, all in the names of Parmerter, et al., and all also issued Jul. 1, 1969; 3,459,731, Gramera, et al., issued Aug. 5, 1969; 3,553,191, Parmerter, et al., issued Jan. 5, 1971; 3,565,887, Parmerter, et al., issued Feb. 23, 1971; 4,535,152, Szejtli, et al., issued Aug. 13, 1985; 4,616,008, Hirai, et al., issued Oct. 7, 1986; 4,638,058, Brandt, et al., issued Jan. 20, 1987; 4,746,734, Tsuchiyama, et al., issued May 24, 1988; and 4,678,598, Ogino, et al., issued Jul. 7, 1987, all of the above patents are incorporated herein by reference. Examples of cyclodextrin derivatives suitable for use herein are methyl-beta-cyclodextrin, hydroxyethyl-beta-cyclodextrin, and hydroxypropyl-beta-cyclodextrin of different degrees of substitution (D.S.), available from Amaizo; Wacker Chemicals (USA), Inc.; and Aldrich Chemical Company. Water-soluble derivatives are also highly desirable.

The compositions and articles of this invention optionally contain, in addition to uncomplexed, small particle size cyclodextrins, an effective, i.e., odor-controlling, amount of various additional adjunct odor-controlling materials. Incorporating adjunct odor-controlling materials will enhance cyclodextrin's capacity for controlling odors, as well as the range of odor types being controlled. Such materials include, for example, zeolites, activated carbon, kieselguhr, and water-soluble antibacterial compounds, such as cetyl pyridinium chloride, zinc chloride, copper salts, copper ions, chlorhexidine, quaternary ammonium compounds, chelating agents, parabens, chitin, pH buffered materials, and the like. Especially preferred is zeolite material having "intermediate" silicate/aluminate ratios.

A wide variety of intermediate zeolites suitable for use herein are commercially available as VALFOR CP301-68, VALFOR 300-63, VALFOR CP300-35 and VALFOR CP300-56, from PQ Corporation, and the CBV100 series (other than Mordenite, as noted below) of zeolites from Conteka.

In the event the zeolites herein are optionally to be used in conjunction with the activated carbon, it is preferred (for visually aesthetic purposes) to coat the carbon with the zeolite using a binder.

Other odor-controlling agents include kieselguhr, and water-soluble antibacterial compounds, such as cetyl pyridinium chloride, zinc chloride, copper salts, copper ions, chlorhexidine, quaternary ammonium compounds, chelating agents, parabens, chitin, pH buffered materials, and the like.

The encapsulated agents ingredients and compositions, i.e., perfumes, of this invention are the conventional ones known in the art. Selection of any encapsulated agents component, or amount of encapsulated agents, is based on functional and aesthetic considerations. Preferred encapsulated agents components useful in the present invention are the highly volatile, and the moderately volatile encapsulated agents ingredients, more preferably the highly volatile, low boiling ingredients.

The highly volatile, low boiling, encapsulated agents ingredients typically have boiling points of about 250° C. or lower. These highly volatile encapsulated agents ingredients are fleeting and are quickly lost as they are released. Many of the more moderately volatile encapsulated agents ingredients are also quickly lost. The moderately volatile encapsulated agents ingredients are those having boiling points of from about 250° C. to about 300° C. Many of the encapsulated agents ingredients as discussed hereinafter, along with their odor characters, and their physical and chemical properties, such as boiling point and molecular weight, are given in "Encapsulated agents and Flavor Chemicals (Aroma Chemicals)," Steffen Arctander, published by the author, 1969, incorporated herein by reference.

Examples of the highly volatile, low boiling, encapsulated agents ingredients are: anethole, benzaldehyde, benzyl acetate, benzyl alcohol, benzyl formate, iso-bornyl acetate, camphene, cis-citral (neral), citronellal, citronellol, citronellyl acetate, para-cymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, alpha-pinene, beta-pinene, gamma-terpinene, alpha-terpineol, beta-terpineol, terpinyl acetate, and vertenex (para-tertiary-butyl cyclohexyl acetate). Some natural oils also contain large percentages of highly volatile encapsulated agents ingredients. For example, lavandin contains as major components: linalool; linalyl acetate; geraniol; and citronellol. Lemon oil and orange terpenes both contain about 95% of d-limonene.

Examples of moderately volatile encapsulated agents ingredients are: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, and veratraldehyde. Cedarwood terpenes are composed mainly of alpha-cedrene, beta-cedrene, and other $C_{15}H_{24}$ sesquiterpenes.

The encapsulated agents/cyclodextrin inclusion complexes of this invention are formed in any of the ways known in the art. Typically, the complexes are formed either by bringing the encapsulated agents and the cyclodextrin together in a suitable solvent, e.g., water, or, preferably, by kneading/slurrying the ingredients together in the presence of a suitable, preferably minimal, amount of solvent, preferably water. The kneading/slurrying method is particularly desirable because it results in smaller particles so that there is less, or no, need to reduce the particle size. In addition, less solvent is needed and therefore less separation of the solvent is required. Disclosures of complex formation can be found in Atwood, J. L., J. E. D. Davies & D. D. MacNichol, (Ed.): Inclusion Compounds, Vol. III, Academic Press (1984), especially Chapter 11, Atwood, J. L. and J. E. D. Davies (Ed.): Proceedings of the Second International Symposium of Cyclodextrins Tokyo, Japan, (July, 1984), and J. Szejtli, Cyclodextrin Technology, Kluwer Academic Publishers (1988). The publications are hereby incorporated herein by reference.

Microcapsules 70 for use in this invention can be made by many of several well-known encapsulating processes. Examples of appropriate processes include chemical encapsulating processes and mechanical encapsulating processes. A wide variety of processes exist by which the microcapsules herein can be manufactured. These varied processes provide different techniques for producing microcapsules of varying sizes, alternative materials for the composition of the capsule shell and various different functional materials within the shell. Some of these various processes are shown in U.S. Pat. Nos. 3,516,846; 3,516,941; 3,996,156; 4,409, 156 and 5,180,637 and British patent specification Nos. 1,156,725; 2,041,319 and 2,048,206, and each is incorporated herein by reference.

It is also desirable to have microcapsule construction resist the effects of variable ambient conditions. It is therefore desirable that rupture strength exceed 4.0 g/cm after storage at 120° C. and less than 1% R.H. for seventy-two hours. This test would be performed by storage in an oven, removal to a neutral environment (e.g., sealed bag or jar) until the article is at room temperature, and then measuring the rupture strength. It is preferred that the rupture strength is at least 8.0 g/cm and most preferred that the rupture strength is at least 16 g/cm under those conditions. The article must still display a rupture strength between 2 and 90g/cm at 20° and 50% R.H. The use of microcapsules 70 which are not moisture sensitive in combination with these large microcapsules 70 (i.e., greater than 30 microns and up to 50 microns) provides a useful microcapsule-containing adhesive layer.

An example of a mechanical encapsulating process is the impingement of droplets of the material to be encapsulated (i.e., in the case of this invention, encapsulated agents or other deodorant composition) within liquid or semi-solid films of intended capsule wall material; separation of the thereby encapsulated droplet from the film of impingement; and solidification of the microcapsule wall material.

Chemical encapsulating processes generally include combining a first reactive material in a continuous phase capsule manufacturing vehicle and a second reactive material into droplets to be encapsulated. The droplets are then dispersed in the manufacturing vehicle and a reaction between the reactive materials is effected. Liquid-liquid phase separation of the polymeric capsule wall material from the vehicle is carried out wherein the phase-separated polymeric material wets and enwraps the dispersed droplets to be encapsulated.

A wide variety of different materials may also be used in making the capsule shells. A popular material for shell formation is the polymerization reaction product between urea and formaldehyde or melamine and formaldehyde, or the polycondensation products of monomeric or low molecular weight polymers of dimethylolurea or methylolated urea with aldehydes. A variety of capsule forming materials are disclosed, for example, in U.S. Pat. Nos. 3,516,846 and 4,087,376 and British patent specification Nos. 2,006,709 and 2,062,570, and each is incorporated herein by reference.

It has also been found that microcapsule size plays a role in the usefulness of microcapsules herein according to the practice of the present invention. Generally the microcapsules should have an average diameter between 5 and 100 microns and preferably between 12 and 30 microns when the capsule payload is between 80 and 90% by weight of the total capsule weight. It is highly preferred that microcapsules herein have an average diameter between 14 and 42 microns and it is most preferred that the microcapsules have a diameter between 15 and 25 microns. These dimensions play a surprisingly important role in the ability to control the percentage of rupture of microcapsules in the practice of the present invention. With lower payloads (e.g., 70–80%), the microcapsules should be larger to provide the necessary rupture strength. The broadest range of average capsule size under most conditions would be about 5 to 100 microns. When 8 micron microcapsules are used, a 90–95% by weight payload is preferred. Generally preferred are microcapsules having sizes of between 8 and 30 micrometers.

Microcapsules herein can form between 20 and 99 percent by volume of the total binder composition of the perfume zone 85, but most preferably between 30 and 75 percent of this total composition volume. The absolute peel force tends to be dependent on the weight of the base coat and relatively independent of the amount of microcapsules (up to 50% by weight of microcapsules 70 per unit area).

It is preferred that microcapsules herein have an average diameter between 5 and 100 micrometers, the cohesive strength of the adhesive composition layer being less than the strength of the bond between the binder and the coated surface of the perfume zone 85, the tensile rupture strength of the microcapsules being less than the cohesive strength of the binder, and the rupture force of the microcapsule containing binder at 50% relative humidity being between at least 0.5 ounces per linear five-and-one half inches (greater than 1.0 g/cm and less than 20 g/cm). It is preferred that the rupture strength of the microcapsules exerted by a pull-strip 80 exceeds 2.0g/cm and is less than 16 g/cm and most preferably exceeds 2.5 g/cm and is less than 10 g/cm.

In most preferable embodiments, the nature and composition of the binder is not critical to the practice of the invention as long as the binder is capable of bonding the microcapsules 70 to the backsheet outer surface 52 or backing member 88. Also, it should be noted that a suitable binder for the practice of the invention herein will not stick to or otherwise soil clothing when a perfume zone 85 has been uncovered and subsequently placed in close proximity to clothing. The quantity of adhesive must be sufficient to hold the microcapsules in place one of the above mentioned surfaces until rupture of the microcapsules at removal of the diaper 20 from the wearer. Any class of adhesives including but not limited to polyurethane's, polyacrylates, polyvinyl resins (e.g., polyvinyl alcohol, polyvinyl chloride), polyamides, polyesters, polyolefins, starches, gum arabic, gelatin and the like may be readily used in the practice of the present invention.

Preferably, the binder 82 used to secure the release agents 65 contained therein to the perfume zone surface 85 and the pull-strip 80 is an acrylate- or methacrylate-based adhesive system comprising infusible, solvent dispersible, solvent insoluble, inherently tacky, elastomeric copolymer microspheres as disclosed in U.S. Pat. No. 3,691,140. Alternatively, this adhesive composition may comprise hollow, polymer, acrylate, infusible, inherently tacky, solvent insoluble, solvent dispersible, elastomeric pressure-sensitive adhesive microspheres as disclosed in U.S. Pat. No. 5,045,569. Washing of the microcapsules 70 before mixing them with the adhesive often tends to provide more consistency in their properties by removing low molecular weight, unreacted materials.

In another aspect, the present invention involves a novel article comprising a thermoplastic, preferably flexible, substrate having partially embedded therein rupturable microcapsules. In this embodiment, binder resin is required. This article can be used in situations where good retention and protection of microcapsules is required, but where access to the microcapsules must be retained. Methods for applying the binder (with microcapsules) to the substrate can vary, depending upon available methods and economics more than any other parameter. Suitable application methods include air knife, gravure coating, and printing methods including silk screening, gravure, and flexographic techniques. The binder (with microcapsules) may be applied either in a continuous or discontinuous pattern on the backsheet outer surface or backing member.

Capsule wall materials suitable for use in accordance with the teachings of this invention include any appropriate polymeric film-forming material. For example, microcapsules may be made from natural hydrophilic polymeric materials such as gelatin, gum arabic, starch, carrageenin, and zein; natural polymeric materials modified in some way such as ethyl cellulose, carboxymethyl cellulose, shellac, resin and nitrocellulose; and other polymeric materials such as polyvinyl alcohol, polyethylene, polystyrene, polyacrylamide, polyether, polyester, polybutadiene, silicone, epoxy and polyurethane.

The particular encapsulated agents or deodorant encapsulated forms no part of this invention and may be varied to so great a degree as to defy classification or description. Reference is made, instead, to "Cosmetics, Science and Technology," second edition, edited by M. S. Balsam and Edward Sagarin and published by John Wiley & Sons, Inc., of N.Y. 1972. In particular, reference is made to Chapter 32, "Fragrance" written by M. S. Balsam for examples of the variety of encapsulated agents formulations possible.

The material contained in the microcapsules herein can be any of a variety of liquids, including solutions, dispersions, and gelled materials. Preferred types of ingredients are organic solids which are fragrance-releasing materials that readily volatilize upon rupture of the microcapsules. The most preferred types of ingredients would be fragrant materials (such as essences and most preferably medium to highly volatile perfumes) or materials which provide chemically active vapors or liquids (e.g., bacteriostats or deodorants). Whatever the fragrance, it or they should be chosen to be compatible with the perfume zone 85, binder 82, and pull-strip 80 and all other diaper components.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A diaper having a rear waist region, a front waist region opposed to said rear waist region and a crotch region positioned between said rear waist region and said front waist region, said diaper being adapted to fit about the lower torso of a wearer when worn for the collection of urine and solid exudates, the diaper comprising:
   a liquid pervious topsheet;
   a liquid impervious backsheet being joined to said topsheet, said backsheet having an inner surface and an outer surface;
   an absorbent core located between said topsheet and said backsheet; at least one perfume zone located on said outer surface of said backsheet, said perfume zone comprising a pull-strip and a binder securing said pull-strip to said outer surface of said backsheet, said binder comprising release agents dispersed therein for the release of perfume; and
   a fastening system comprising a first fastening member having a pair of fastening tabs disposed in said rear waist region of said diaper and a second fastening member disposed in said front waist region of said diaper, said first fastening members being attachable to said second fastening member about the torso of said wearer to maintain said diaper about said wearer.

2. The diaper of claim 1 wherein said release agents are microcapsules.

3. The diaper of claim 1 wherein said release agents comprise perfume selected from the group consisting of uncomplexed cyclodextrins, perfumes, zeolites, activated carbons and mixtures thereof.

4. The diaper of claim 1 wherein a number of said release agents provide steady-state diffusion of perfume released over time at detachment of said pull-strip from said binder without rupture of said steady-state release agents.

5. The diaper of claim 1 wherein a number of said release agents provide a fragrance burst at detachment of said pull-strip from said binder.

6. The diaper of claim 1 wherein a number of said release agents provide a steady-state release of perfume over time without rupture of said steady-state release agents and a number of said release agents provide a fragrance burst at detachment of said pull-strip from said binder, said fragrance burst release agents rupturing at said fragrance burst of said perfume.

* * * * *